United States Patent [19]

Dedolph

[11] Patent Number: 5,744,424
[45] Date of Patent: Apr. 28, 1998

[54] PLANT GROWTH PROMOTER COMPOSITION COMPRISING N-6-BENZYLADENINE, AN ALCOHOL, AND A METAL HYDROXIDE

[75] Inventor: Richard R. Dedolph, Taylorsville, Ky.

[73] Assignee: Caudill Seed Company, Inc., Louisville, Ky.

[21] Appl. No.: 538,015

[22] Filed: Oct. 2, 1995

Related U.S. Application Data

[63] Continuation-in-part of Ser. No. 160,736, Dec. 3, 1993, Pat. No. 5,455,220.

[51] Int. Cl.$^6$ .................. A01N 25/02; A01N 25/22; A01N 43/90
[52] U.S. Cl. .................. 504/241; 71/DIG. 1
[58] Field of Search .................. 504/241; 71/DIG. 1

[56] References Cited

U.S. PATENT DOCUMENTS

| | | | |
|---|---|---|---|
| 3,630,710 | 12/1971 | Frederickson | 71/23 |
| 3,893,855 | 7/1975 | Charkoudian | 96/3 |
| 3,985,536 | 10/1976 | Abbe et al. | 71/24 |
| 4,264,704 | 4/1981 | Borror et al. | 430/224 |
| 4,326,877 | 4/1982 | Kazutoyo | 71/92 |
| 4,387,155 | 6/1983 | Hill et al. | 430/217 |
| 4,489,152 | 12/1984 | Oberhauser et al. | 430/229 |
| 4,581,056 | 4/1986 | Noodén et al. | 71/28 |
| 4,666,497 | 5/1987 | Tenzer | 71/6 |
| 4,902,332 | 2/1990 | Elliott et al. | 71/76 |

*Primary Examiner*—S. Mark Clardy
*Attorney, Agent, or Firm*—Middleton & Reutlinger; David W. Carrithers

[57] ABSTRACT

Composition for the regulation and promotion of the growth rate and characteristics of a variety of plants by providing a method for increasing the concentration of N-$^6$-Benzyladenine in a concentrated solution of a solubilizing agent including a selected alcohol(s) or hydroxy compound (s), such as a glycol and a selected hydroxide. Included is a method of preparing a plant growth promoter concentrate from stable water dilutable liquid concentrates of $N^6$Benzyladenine, ("$N^6$BA").

A process of increasing iron absorption by plants utilizes a method of uniformly coating dry powdered humic acid and seaweed with a $N^6$BA concentrate solution by preparing a solution of $N^6$BA concentrate solution comprising an alcohol and an alkaline metal hydroxide, applying the $N^6$BA concentrate solution to a mixture of dry powdered humic acid and seaweed, evaporating the residual alcohol through low temperature drying forming a caked material, pulverizing the caked material to a powdered form, and suspending the finely powdered concentrate in an aqueous spray solution.

19 Claims, 5 Drawing Sheets

SOLUBILITY OF N-6-BENZYLADENINE
IN VARIOUS NORMALITIES
OF POTASSIUM HYDROXIDE
IN 95% ETHYL ALCOHOL

SOLUBILITY OF N-6-BENZYLADENINE
IN VARIOUS NORMALITIES
OF POTASSIUM HYDROXIDE
IN 95% ETHYL ALCOHOL

SOLUBILITY OF N-6-BENZYLADENINE IN VARIOUS NORMALITIES OF POTASSIUM HYDROXIDE IN WATER

\* $N^6BA$ DISSOLVED IN ETHANOL WITH ALKALINE METAL.

FIG. 5

PLANT GROWTH PROMOTER COMPOSITION COMPRISING N-6-BENZYLADENINE, AN ALCOHOL, AND A METAL HYDROXIDE

BACKGROUND OF THE INVENTION

This application is a continuation-in-part application of Ser. No. 08/160,736 filed on Dec. 3, 1993, now U.S. Pat. No. 5,455,220.

TECHNICAL FIELD

This invention relates to the general area of increasing the physiological efficacy of agricultural fertilizers applied to plants. More particularly, the present invention relates to liquid compositions including $N^6$-Benzylaminopurine or $N^6$-Benzyladenine (hereinafter $N^6BA$), for the purpose of promoting the growth and development of a wide variety of plant life and as a plant growth regulator. The method provides a means for preparing very stable water dilutable liquid concentrates of $N^6BA$ and increasing the solubility of $N^6BA$ providing a means for creating highly concentrated solutions of $N^6BA$.

BACKGROUND OF THE INVENTION $N^6BA$ has been recognized as an agent for promoting the growth and development of various types of plant life and is also used in some discrete, nonliving, chemical processes. $N^6BA$ has also generally ben demonstrated as physiologically effective in modifying plant growth and development of a myriad of plant species in many different ways. Responses elicited include promotion of cell division, inhibition of respiration, increasing retention of water and drought resistance, enhancing root and top growth with change in root/top ratios as well as shortening plant internodes which produces shorter bushier plants. The material has also been found to increase plant sugar content and enhancing color development and intensity in fruits and flowers while increasing the numbers of flowers.

Moreover, application of the material can increase chlorophyll retention in both pre and post harvest commodities and extends useable storage life of many fresh commodities while imparting a greater resistance to environmental stress. The advantages of $N^6BA$ may be obtained by aqueous spray application of $N^6BA$ at low concentrations to field or greenhouse grown plants or as an aqueous dip applied to harvested commodities. $N^6BA$ may also be applied to preplanted seeds.

The major impediment to the wide spread use of this growth regulating compound has been the lack of a stable liquid concentrate. When this is coupled with the extreme difficulties in solubilizing $N^6BA$, it constitutes a major impediment to it's use. Working concentrations can be attained for spray applications but considerable difficulty is experienced in attaining such field useable concentrations because of the low solubility of $N^6BA$ in known acceptable solvents. The low solubility ratios of $N^6BA$ has severely restrained its widespread use. The difficulty of compounding concentrates for use in forming dilute spray solutions has severely limited widespread field use and generally relegated the use of the material to scientific investigation In order to be effective, $N^6BA$ must be applied to the plant substrate as a dilute solution. However, general use of $N^6BA$ has been restricted due to the difficulty encountered in preparation of low characteristic solubility of the material in water or other carries. For example, at about 15° C., the solubility of $N^6BA$ in water is limited to about 0.00044 grams per 100 milliliters which is far below a realistically useful level for commercial use.

$N^6BA$ is virtually insoluble in water. It is known that the solubility of $N^6BA$ can be increased by the use of metal hydroxide in the water. The solubility of the $N^6BA$ in a metal hydroxide water solution depends greatly upon the solubility of the metal hydroxide in water, specifically upon the normality of the solution. Even in such compositions the solubility is not increased to concentration levels practical for field concentrates and is not useful at all for super concentrates required for effective commercial use. Preparation of a super concentrate would reduce packaging and shipping cost. The super concentrate could then be diluted to field concentrate levels with further dilution before application.

$N^6BA$ may be dissolved to approximately 5 percent concentration in mineral acids which are difficult to handle and are often inappropriate solvents for agricultural use. $N^6BA$ can also be dissolved in alcohol-mineral acid solvent systems; however, the solubility cannot be increase beyond the solubility of the undiluted mineral acid.

SUMMARY OF THE INVENTION

The present invention provides means for the formulation of concentrated compositions of $N^6BA$ which allow the material to be packaged and shopped in commercially practical quantities.

The present invention provides compositions for the regulation and promotion of the growth rate and characteristics of a variety of plants including $N$-$^6$-Benzyladenine in a solubilizing agent which includes a selected alcohol(s) or hydroxy compound(s) such as a glycol and a selected hydroxide.

More particularly, the present invention provides a means for dramatically increasing the solubility of $N^6BA$ in a solution of both alcohol or organic mono or polyhydroxy compounds such as a glycol or glycerine in combination with a hydroxide. For example, solutions of up to approximately 50 percent $N^6BA$ can be formulated in a selected alcohol, such as ethanol, methanol, ethylene glycol, or polyethylene glycol and a metal hydroxide soluble in the selected alcohol and/or water solution. Such a solution provides commercially effective concentrations as stock solutions which can be produces and shipped for subsequent dilution and for consumer, field, or green house application.

Comparing the solubilities of metal hydroxides in water focuses attention upon potassium hydroxide, "KOH", and sodium hydroxide, "NaOH", saturated solutions which yield normalities of 18.0 and 21.0 respectively. Calcium, magnesium, and zinc hydroxides, alkaline earth metals, ate saturation, yield normalities of 9.6, 8.2, and 9.4 respectively, all at 18° C. The present invention is directed toward using solutions of hydroxides of alkaline metals such as sodium and potassium but is workable using hydroxides of alkaline earth metals such as calcium, magnesium, and zinc.

Moreover, the present invention includes a process of increasing iron absorption by plants utilizes a method of uniformly coating dry powdered humic acid and seaweed with a $N^6BA$ concentrate solution by preparing a solution of $N^6BA$ concentrate solution comprising an alcohol and an alkaline metal hydroxide, applying the N6BA concentrate solution to a mixture of dry powdered humic acid and seaweed, evaporating the residual alcohol through low temperature drying forming a caked material, pulverizing the caked material to a powdered form, and suspending the finely powdered concentrate in an aqueous spray solution.

Examples of solutions within the scope of the present invention are described hereinafter and graphically illustrated but it will be understood that the compositions discussed herein are not be way of limitation and that other compositions also within the scope of the present invention will occur to those skilled in the art upon reading the disclosure set forth hereinafter.

DETAILED DESCRIPTION OF THE PREFERRED EMBODIMENT

Figure 1:
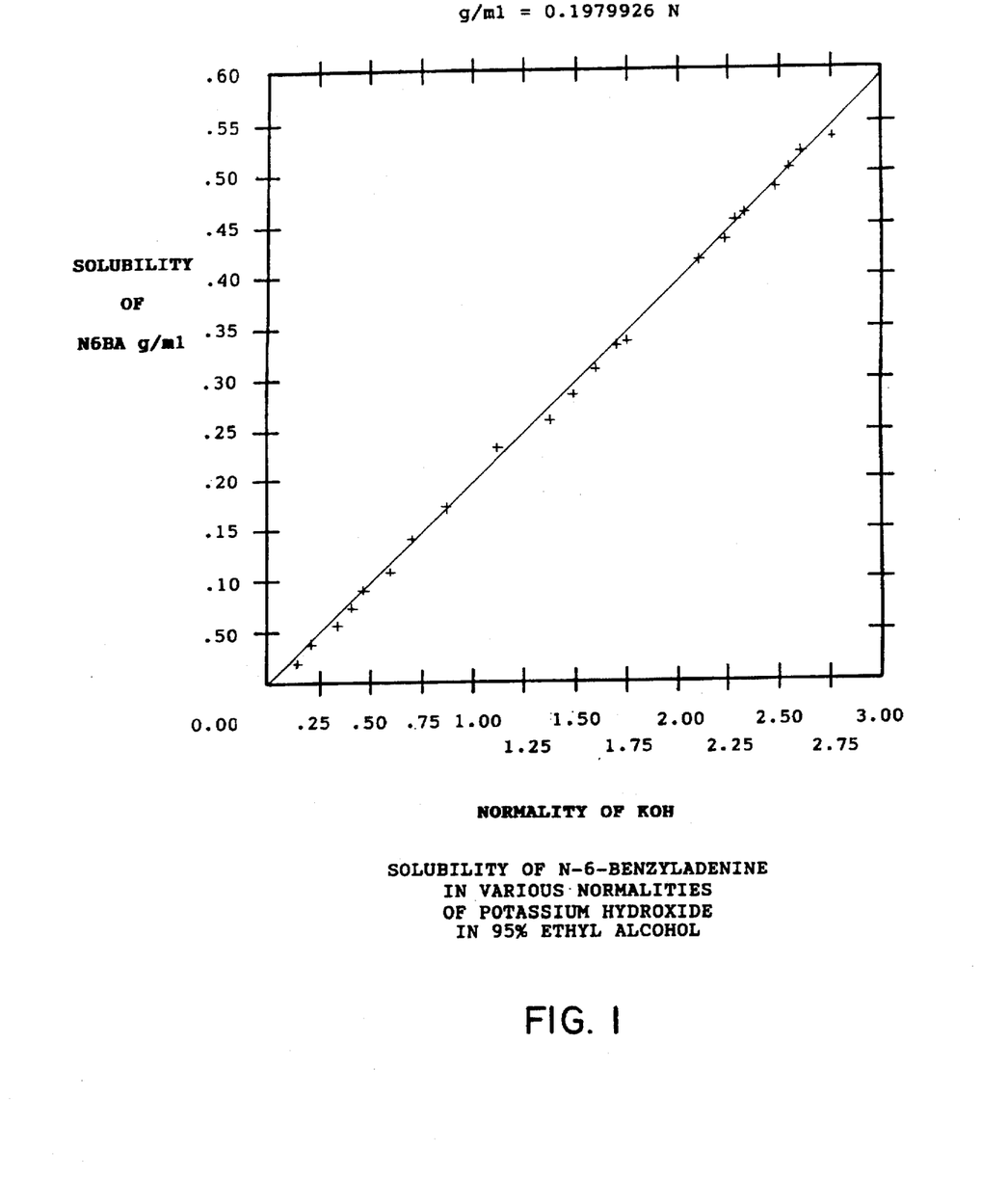
FIG. 1 shows the solubility of $N^6BA$ in various normalities of potassium hydroxide in 95% ethyl alcohol.
Figure 2:
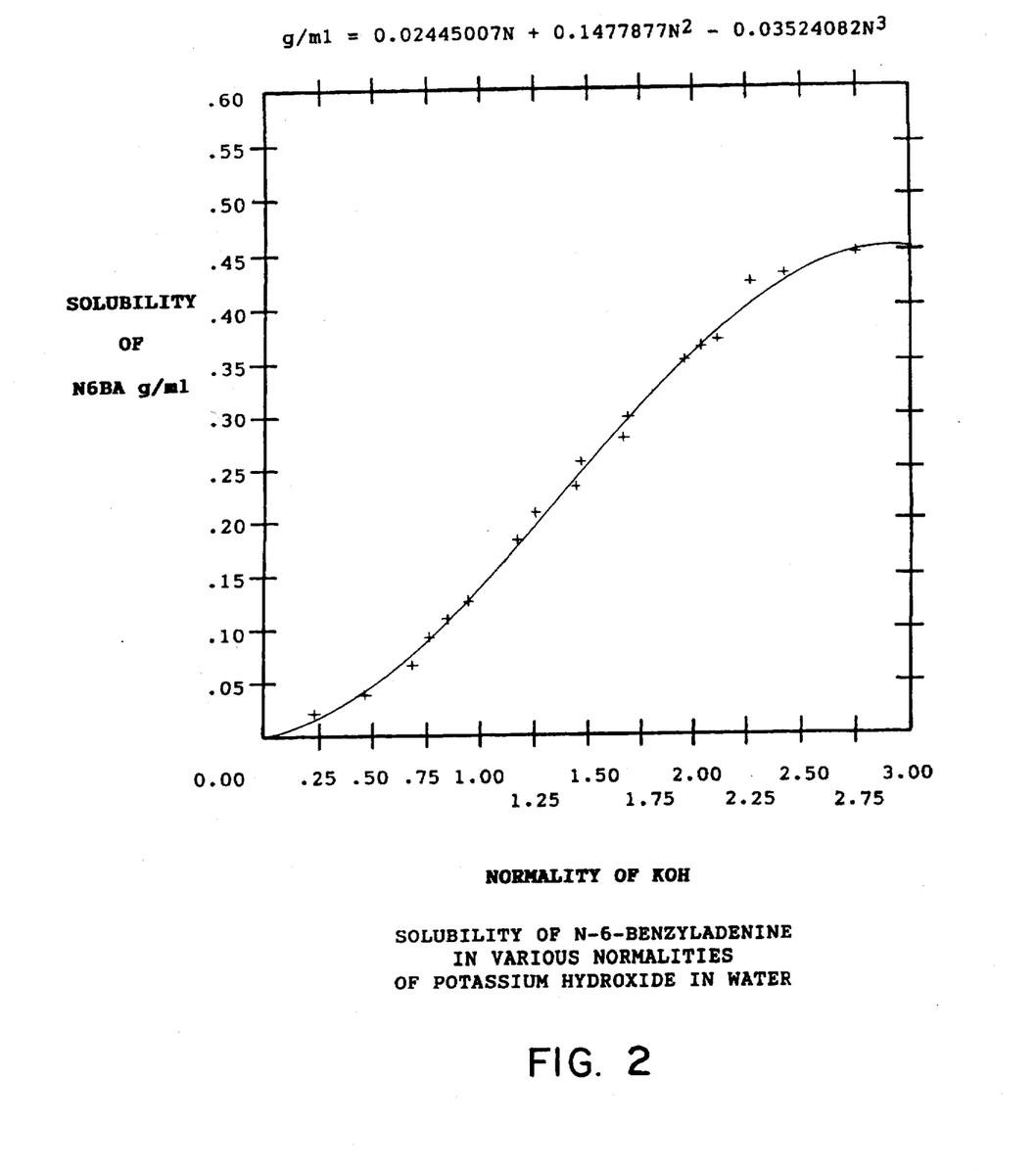
FIG. 2 shows the solubility of N6BA in various normalities of potassium hydroxide in 95% water.

When $N^6BA$ is dissolved in a solution, the volume of the solution is increased, and its normality correspondingly decreased. With equinormal solutions of $N^6BA$ in water and $N^6BA$ in 95% ethanol it is apparent that the $N^6BA$ is more soluble in a 95% ethanol potassium hydroxide solution, as shown in FIG. 1 than in a water potassium hydroxide solution as shown in FIGS. 2. The natures of the solubilization is quite different when a potassium hydroxide in 95% ethanol solution is used as illustrated in FIG. 1. The increased solubility is defined by g/m=0.198N. When potassium hydroxide in water is used as the solvent the solubility of the $N^6BA$ with increased normality of the solution is defined by a cubic function described by: $(g/ml=0.0243N+0.14779N^2-0.03524082N^3$, where g/ml is the grams of $N^6BA$ soluble in the potassium hydroxide solution and "N" the normality of the solution.

The solubility data enable address a second underlying problem encountered when the aqueous hydroxide solution is employed. Using the solubility of $N^6BA$ in aqueous solutions of various normalities as shown in FIG. 1, it is noted that the normality of a concentrate of $N^6BA$ is insufficient to maintain the solubility of the $N^6BA$ at a lower concentration reached by water dilution of a more concentrated saturated aqueous solution as shown in Table 1.

TABLE 1

The required normality of a potassium hydroxide solution for solubility of N-6-benzyladenine at common spray or drench concentrations and the normality of such N-6-Benzyladenine solutions after dilution of a concentrate of various concentrations.

| SPRAY CONCENTRATION AND REQUIRED NORMALITY FOR SOLUBILITY | PERCENT AND PPM N-6-BENZYLADENINE IN CONCENTRATE ||||| 
|---|---|---|---|---|---|
| | 10% | 20% | 30% | 40% | 50% |
| WATER SOLVENT AND DILUENT ||||||
| PPM | 100,000 | 200,000 | 300,000 | 400,000 | 500,000 |
| | .0821* | 1.280* | 1.721* | 2.250* | |
| 250 | **52 | **39 | **34 | **34 | |
| 0.0096 | 0.0021 | 0.0016 | 0.0014 | 0.0014 | |
| 500 | **102 | **131 | **72 | **69 | |
| 0.0185 | 0.0041 | 0.0052 | 0.0029 | 0.0028 | |
| 1000 | **210 | **162 | **144 | **141 | |
| 0.0342 | 0.0082 | 0.0064 | 0.0057 | 0.0056 | |
| 1500 | **322 | **253 | **220 | **215 | |
| 0.0480 | 0.0123 | 0.0098 | 0.0086 | 0.0084 | |
| 2000 | **439 | **336 | **299 | **231 | |
| 0.0600 | 0.0164 | 0.0128 | 0.0115 | 0.0090 | |
| 95% ETHANOL SOLVENT - WATER DILUENT ||||||
| | 100,000 | 200,000 | 300,000 | 400,000 | 500,000 |
| | 0.5051* | 1.101* | 1.515* | 2.020* | 2.525* |
| 250 | **250 | **250 | **250 | **250 | **250 |
| 0.0013 | 0.0013 | 0.0013 | 0.0013 | 0.0013 | 0.0013 |
| 500 | **500 | **500 | **500 | **500 | **500 |
| 0.0025 | 0.0025 | 0.0025 | 0.0025 | 0.0025 | 0.0025 |
| 1000 | **1000 | **1000 | **1000 | **1000 | **1000 |
| 0.0051 | 0.0051 | 0.0051 | 0.0051 | 0.0051 | 0.0051 |
| 1500 | **1500 | **1500 | **1500 | **1500 | **1500 |
| 0.0076 | 0.0076 | 0.0076 | 0.0076 | 0.0076 | 0.0076 |
| 2000 | **2000 | **2000 | **2000 | **2000 | *2000 |
| 0.0101 | 0.0101 | 0.0101 | 0.0101 | 0.0101 | 0.0101 |

*Normality required to solubilize
**Concentration in ppm the normality of the diluted solution is the lower number in each boxed data set The normality of the hydroxide solution employed in the concentrate might be raised to accommodate the shortcoming of an aqueous solvent. However, in practice $N^6BA$ is applied as a drench or spray chemical. As with any spray chemical, concentrated basic or acidic formulations must be avoided to limit foliage damage.

The advantages afforded by the present invention using about 95% ethanol a solvent provides a maintenance of normality with dilution. Normality is constant regardless of dilution of any of the concentrates of any strength to a spray concentrate level. The required normality is not only provided for by the concentrate but is far less than that required when water is used as the solvent as shown in Table 1.

When 95% ethanol is used as a solvent, not only is the $N^6BA$ far more soluble in the 95% ethanol at any normality as indicated in Table 1 and FIGS. 1 and 2, but once solubilized, it remains in solution despite high levels of dilution with water. The constant normality using the 95% ethanol solution is a factor but not the sole governing factor for it can be shown that a 40% solution diluted 800:1 with water to form a 500 ppm concentration will remain soluble at a normality of 0.0025. Were water the solvent starting with dry $N^6BA$ and KOH, a solution concentration of only 62 ppm could be maintained at this normality.

The maximum solubility of $N^6BA$ in the aqueous solution at 20° C. is about 45.5% at 2.875N the corresponding maximum solubility of N⁶BA in 95% ethanol is about 54% at a normality of 2.762. The lack of utility of N⁶BA in water solutions derives from the high normality required to effect solubility in low application ranges and the inadequacy of KOH in water concentrates if used to form stable solutions of lower concentrations by water dilution.

Concentrates of 95% ethanol based solution s may be water diluted and will form stable solutions. The normality of these stable solutions is far lower than that in the water solvent counterparts. The lower normality of the ethanol based spray solutions substantially reduces foliage damage. Controlled horticultural experiments further show dramatic increases in biological response from the product made using ethanol as a concentrate solvent when compared to sprays using water as the sole solvent.

The marked difference in solubilization behavior between water and 95% ethanol solutions is reflected in physical differences in the two sorts of solutions. The 95% ethanol solution is far more viscous than the water based solution. At 45% concentrations and 21° C. Temperatures, the viscosities were found to be 18,800 and 2,800 centipoise, respectively. The approximate density of the water solvent solution at saturation is 1.181 that of the ethanol solvent at saturation 1.083 solution. It has further been found that glycerol or polyethylene glycol both having reactive hydroxyl groups may be used as solvents but that the water must be added to them to effect solubility of the hydroxide and the attendant dissolution of the N⁶BA in these solvents.

It has been shown with these further studies that dissolution of N⁶BA in other than a hydroxide water solution requires the use of a water miscible organic compound with reactive OH groups; and mineral hydroxide; and some water. The 95% ethanol, potassium hydroxide combination is the preferred embodiment of this invention due to economic considerations and proven utility of this combination.

In another embodiment, ammonium hydroxide was used with N⁶BA. The solution was unstable; however, it is anticipated that ammonium hydroxide may be combined with potassium or sodium hydroxide to maintain the required stability.

In one example in accordance with the present invention, it was unexpectedly found that the solubility of N⁶BA in alcohol, in this case ethanol, was directly affected by the addition of quantities of a hydroxide soluble in the alcohol. Potassium Hydroxide was utilized as the selected soluble hydroxide which was added as a co-solute or by predissolution in the alcohol solution. The solubility of the N⁶BA in the alcohol/hydroxide solution was directly proportional to the normality of the solution. An empirical relationship was developed represented by the following equation:

Percent S=(16.7)(N)

where Percent "S" is the per unit volume of N⁶BA expressed as a percentage and "N" is the Normality of the solution after dissolution of N⁶BA in the solution. The results of the tests are illustrated in FIG. 1.

The data of FIG. 1 shows that a direct concentration relationship exists between the Normality of the alcohol/hydroxide solution and concentration of N⁶BA. In the potassium hydroxide/ethanol system, concentrations of at least 60 percent have been achieved. Normal dilution ranges of the above concentration per liter of a 50 percent solution is sufficient to treat approximately 80 acres of turf or to formulate 83 cubic metes or growth regulator solution; however, very high N⁶BA concentrations are desirable for bulk shipments having a concentration of greater than 50 percent.

Moreover, compositions for the regulation and promotion of the growth rate and characteristics of plants comprising N⁶BA having a concentration of at least two percent is achieved by addition of a water soluble organic hydroxy compound and a selected inorganic hydroxide soluble in a water solution. The increase in solubility of the N⁶BA can be attributed to the combination of the hydroxy compound with the inorganic hydroxide without any additional additives; however, it is contemplated that additional nutrients may be selected for combination with the N⁶BA component for particular applications.

One example in accordance with the present invention shows a highly useful 25 percent solution of N⁶BA can be produced by mixing 250 grams of N⁶BA with 84 grams of potassium hydroxide and diluting to one liter with ethanol.

It has also been determined that monovalent hydroxides such as potassium hydroxide and sodium hydroxide have greater solubility in alcohol than di- or tri, or higher valent hydroxides and are therefore preferable to the higher valent hydroxides. For example, potassium hydroxide is soluble at 14:100 ratio in ethanol and 24:100 ration in absolute ethanol. Other alcohol systems also provide the requisite solubility in combination with hydroxides.

Moreover, a wide variety of water soluble polyhydroxy organic materials in which the hydroxide is soluble can also be used as solubilizing agents for N⁶BA. Satisfactory concentrations of N⁶BA have been achieved using glycols such as glycerine and propylene glycol as well as glycol ethers such as polyethylene glycol so long as the glycol is soluble in water and the hydroxide is also soluble in an aqueous solution of the hydroxy compound.

Using 95% ethanol containing a dissolved metal hydroxide yields stable concentrates which may be diluted with water without precipitation. The ethanol based concentrated solutions of N⁶BA are physically different from corresponding concentration using an aqueous solvent. The alcohol based concentrate is quite highly viscous (18,800 cps, 450,000 ppm, 21° C.) and an amber color compared to a light yellow colored far less viscous (2800 cps, 450,000 ppm, 21° C.) water based concentrate. The alcohol based concentrate requires far less alkaline metal to effect solubilization of a given concentration of N⁶BA than does the comparably concentration of N⁶BA when water based.

From these observations, it appears that the physical properties of N⁶BA with respect to the nature of its solubilization are altered when it is solubilized as an ethanol based concentrate.

When ethanol based concentrates and water based concentrates are compared for physiological activity in diluted spray solutions made from said liquid concentrates. The N⁶BA in the spray solution made from the alcohol based concentrate is greater than that made from the water based concentrate as shown in Table 1.

TABLE 2

| BA Source | BA concentration | Average number of basal shoots |
|---|---|---|
| Control; deionized water | 0 | 0.3 |
| BA powder; dissolved in HCl | 500 | 2.0 |
| BA powder; dissolved in KOH | 500 | 2.7 |
| Caudill BA; predissolved | 500 | 3.2 |

Table 2 shows the average number of basal shoots produced on Spathiphyllum "Petite" treated with 500 ppm of BA. The BA was from different sources and mixed using different methods. There were 10 plants tested at each treatment level.

Since the nature of solubilization of $N^6BA$ in alcohol seemed so vastly different than when solubilized in water, the formation of a dry form of a biostimulant product for turf grass was attempted. An amount of 40% (wt/vol) alcohol based $N^6BA$ was added to dry seaweed and dry humic acid forming a thick slurry. The alcohol was subsequently removed from this slurry by drying and mixing at temperatures less than 60° C. The dried material was then ground to pass through a screen with square 0.007 inch openings. Appropriate amounts of dry ferrous sulphate heptahydrate were then thoroughly mixed with the dried ground slurry so that the ratio and amounts of $N^6BA$ humic acid seaweed were identical to that present in one gallon of liquid spray concentrate.

Liquid sprays were prepared from either solubilized dry powder or from an undried liquid concentrate and applied to field plots of Penncross bentgrass in late November as spray solutions. Judgment rates of plot color were made on the dates indicated through mid January and again four months later.

TABLE 3

| DATE | AVERAGE PERCENT GREENING* ** |
|---|---|
| 12/5/94 | 78 |
| 12/16/94 | 77 |
| 1/13/94 | 78 |
| 4/25/95 | 71 |

*PERCENT OF JUDGED MAXIMUM GREENING POSSIBLE.
**THE DIFFERENCE IN AVERAGE PERCENTAGE GREENING MUST EXCEED 3.9 FOR SIGNIFICANCE AT ODDS OF 1 IN 20.
Table 3 shows the Influence of Date of Observation on Percent Greening of Penncross Bentgrass These color ratings made on the four dates of estimation in this thrice replicated randomized block experiment indicated that this variety of bentgrass maintained its color well into early winter at Blacksburg, Virginia and showed good recovery the following spring. Of greatest import in these data was that the relationship of color ratings in response to iron application was unaffected by date of observation. The interaction between date of observation and spray chemical treatment was virtually absent.

When comparison of greening is made between the various iron levels averaging across all dates of observation as the lack of interaction between date of observation and treatment, the data suggests that $N^6BA$ seaweed and humic acid increases greening without adding iron. Table 4 compares a control and dry source at 0 pounds iron per acre.

TABLE 4

| TREATMENT | POUNDS IRON/ACRE | AVERAGE PERCENT GREENING* ** |
|---|---|---|
| CONTROL | 0 | 60 |
| DRY SOURCE | 0 | 68 |
| DRY SOURCE | 0.5 | 75 |
| DRY SOURCE | 1.0 | 80 |
| DRY SOURCE | 1.5 | 80 |
| DRY SOURCE | 2.0 | 87 |
| LIQUID SOURCE | 0.5 | 83 |

*AVERAGE PERCENT OF MAXIMUM GREENING POSSIBLE.
**DIFFERENCE IN AVERAGE PERCENT GREENING MUST EXCEED 7.4 FOR SIGNIFICANCE AT ODDS OF 1 IN 20.
Table 4. The Effect of Dry and Liquid Concentrate on $N^6BA$, Humic Acid and Seaweed with Varying Levels of Iron on Percent Greening of Penncross Bentgrass.

When comparison is made between dry and wet concentrate bases for spray solution both contain approximately equal amounts of iron.

Iron required in plant nutrition is particularly critical in turf grass, since it is continuously removed by clipping of the grass. Though absorbed by roots primarily in the ferrous form it is transformed to the ferric form for use in plant metabolism. Whether clippings are collected or remain on the turf is inconsequential since iron release from clipping decomposition is too low to accommodate the luxurious green growth required for this crop. Periodic application of iron as a foliar spray is therefore common practice. The most notable effect of iron application is marked, quickly apparent, short term greening of the turf. Once applied, soil iron is often quickly rendered unavailable due to leaching, complexing of iron in unavailable forms with other soil chemicals and from the competition with higher plants for available iron by soil micro flora and micro fauna. To offset these losses in part, iron is often applied in a chelated or sequestered form.

Humic acids due to inherently high chelan exchange capacities 300–500 mg/100 grams dry weight and a high affinity for absorption of iron is often used to extend the physiological activity of spray applied. Ferrous sulphate heptahydrate ($FeSO_4 \cdot 7H_2O$) is the most commonly used iron source in spray chemical application.

In the formulation of spray chemical concentrates the maximum percent iron in the concentrate on a wt/wt basis is about 8% at 21° C. Due to its solubility this limits the practical concentration of iron in liquid spray concentrates to the 5–6% range. Dilution of the concentrates by 15 to 50 fold before spray application is common to prevent fertilizer burn. This makes feasible the application of far higher rates of iron. The solubilization of a dry powder in the spray tank by mixing is the method of choice. Quite simply, the greater liquid volume of the dilute spray makes possible the dissolution of more $FeSO_4 \cdot 7H_2O$ application.

The solubility of iron salts aside when iron is applied with seaweed and humic acid its physiological activity in promoting a greening response with turf grass is apparently increased. This affords one the opportunity to obtain unique insight and comparison of the effect of drying the alcohol alkaline metal solution of $N^6BA$ without drying but with $FeSO_4 \cdot 7H_2O$ present.

These data are particularly instructive when comparison is made between the greening response to dry iron concentrate at 0.5 pounds per acre (75% greening) and that to the spray made from wood concentrate at the same level 83% greening, (Table 4). Since these two spray solutions were identical in all respects excepting form of the concentrate one may infer that iron and $N^6BA$ in the spray solution are actually antagonistic in effect.

If the concentrate is liquid and iron competes for a plant which involves a second common component it would be expected that iron in solutions would compete with $N^6BA$ for such a common site of entrance if both iron and $N^6BA$ were in the spray solution.

In a solution made from a dry concentrate which had been prepared from dry seaweed and humic acid and $N^6BA$ had been added as a highly concentrated coating or solution that had thence dried, there would be no opportunity for such site competition between iron and $N^6BA$, since iron would not be in the soluble state necessary for displacement of $N^6BA$ on the absorption site. Once mixed in a spray solution such absorption site competition would be operative. Should this phenomena be operative a problem is inherently present in interpretation of the grass greening area.

Both iron and $N^6BA$ contribute to greening, iron from promoting chlorophyll formation and $N^6BA$ from inhibiting chlorophyll degeneration. These two effects are confounded in determining what caused the greening of the grass crop observed. The data indicate an 8% increase in greening from application of $N^6BA$ spray made from a dry powder of $N^6BA$ coated seaweed and humic acid. (Compare control and 0 iron/acre dry source).

Comparison of the dry concentrate spray source and the liquid concentrate spray source at the 0.5 pound per acre rate showed that the liquid source was 8% greener than the dry.

Figure 3:
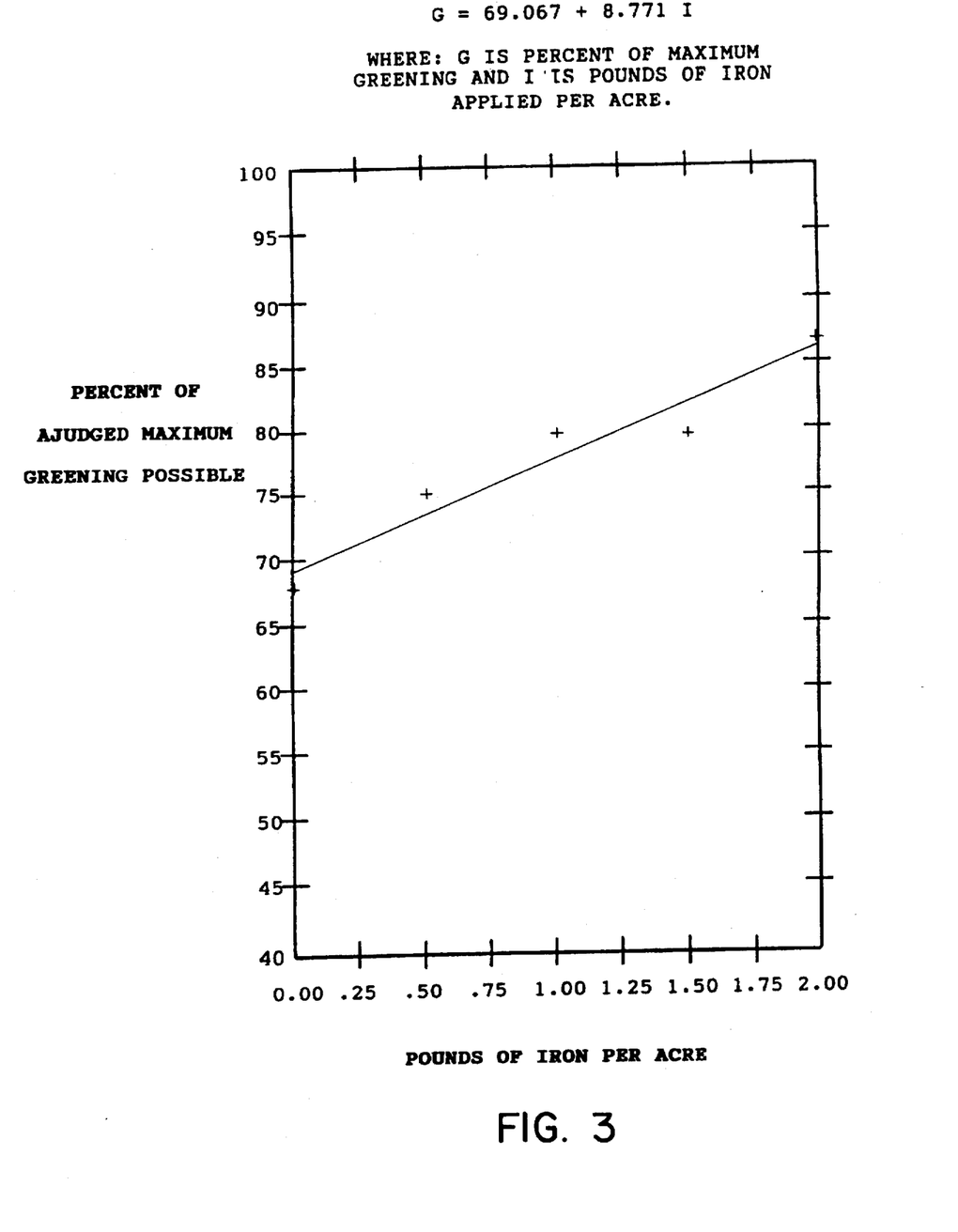
FIG. 3 shows the relationship of percent of maximum greening and per acre iron application in grasses.

The relationship of iron content of dry spray solutions and greening where greening was found to increase with iron concentration in the spray derived from dry concentrate in a linear fashion. Despite a molecular ratio of $N^6BA$ to iron on the order of 1:200 at the 0.5 pound/acre rate of iron application to 1:800 at the 2.0 pound/acre rate. As shown in FIG. 3, the greening data indicates that any inhibition of greening from use of sprays from dry sources may be overcome by using higher concentrations of iron.

Figure 4:
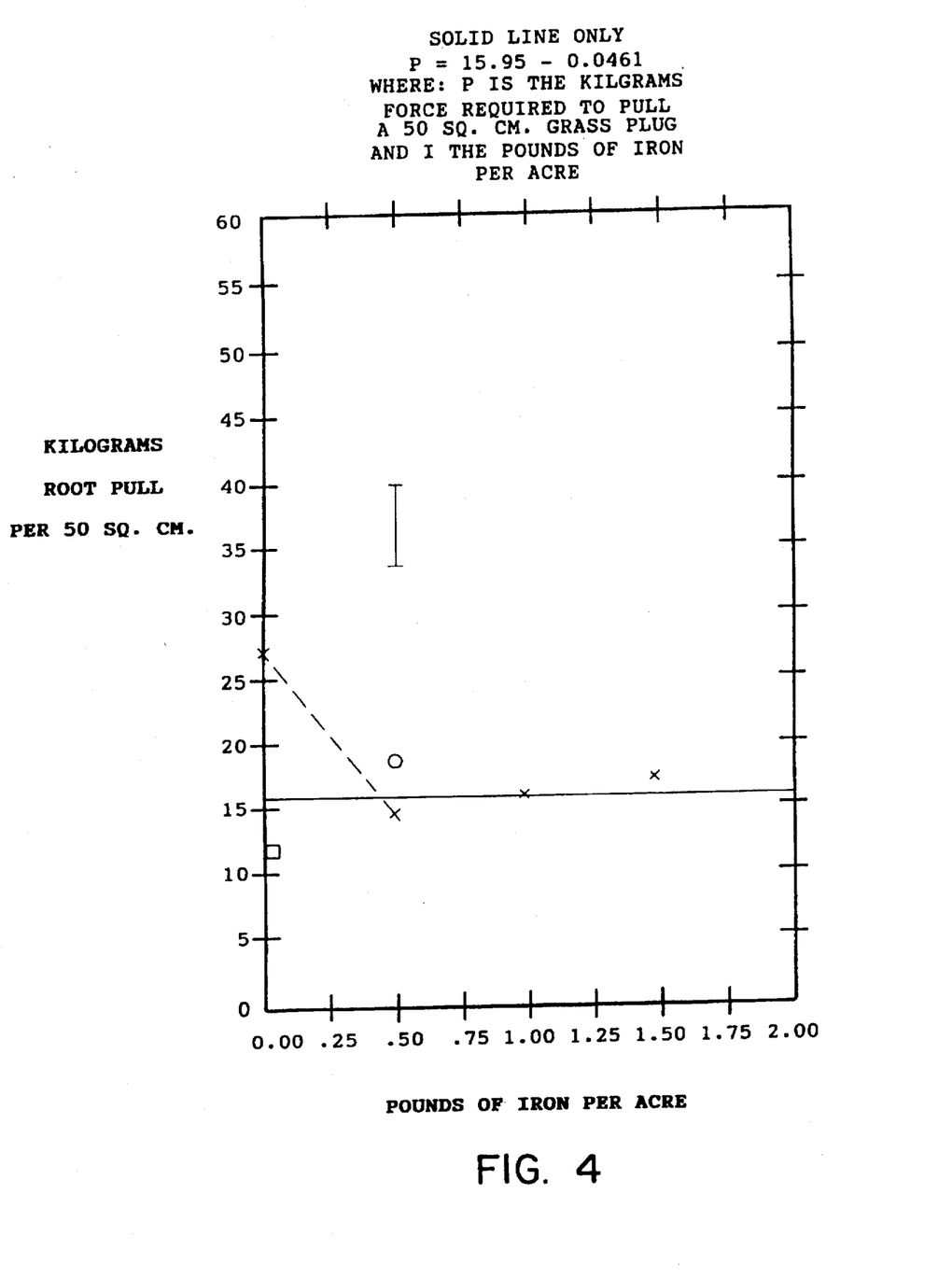
FIG. 4 shows the effect of various levels of iron and $N^6BA$ upon the force required to pull a 50 sq.cm. area grass plug.
Figure 5:
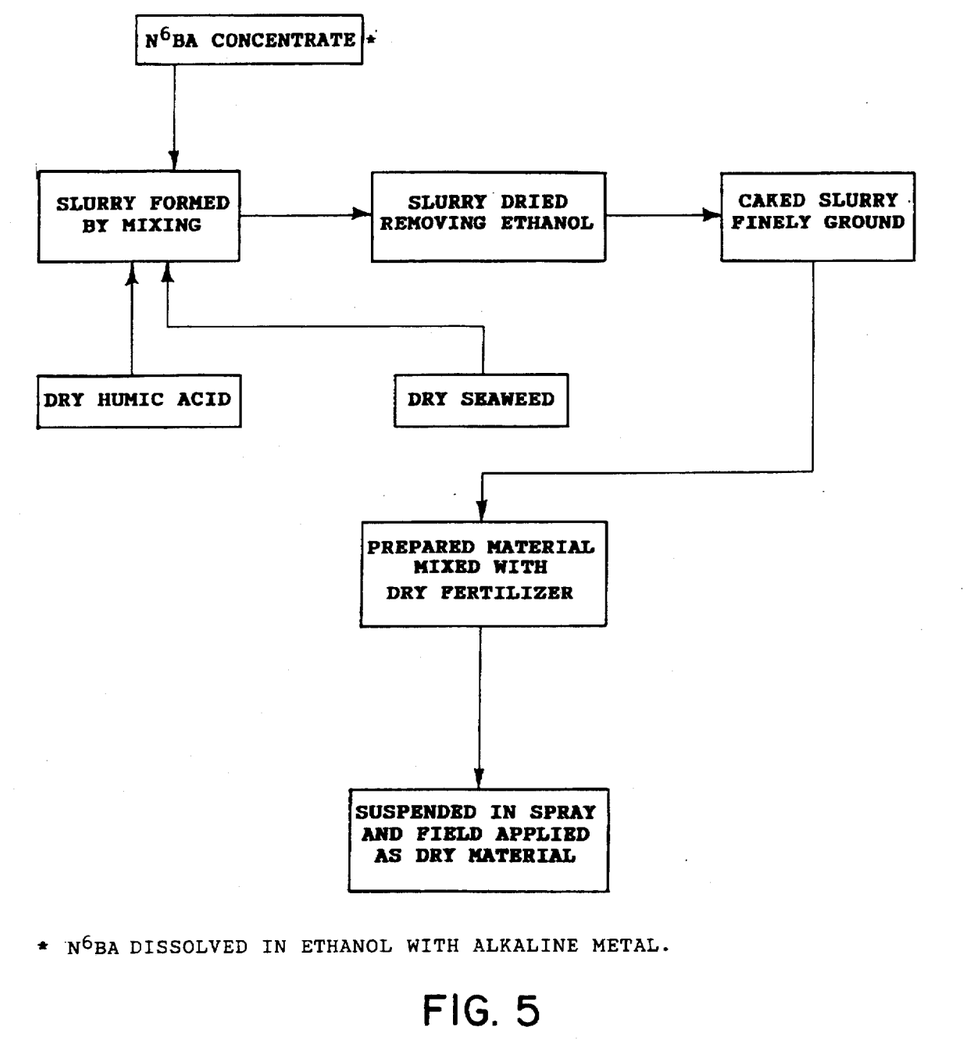
FIG. 5 shows the process of complexing the $NBA^6$ on humic acids and seaweed.

Other more definitive data from root density studies show clearly that the force required for root extraction of sod plugs is substantially decreased by the addition of iron to the dry spray concentrate source spray solutions when iron is added as illustrated in FIG. 4.

These data are particularly telling since only very slight decreases in extraction forces (root densities) are shown in the 0.5–2.0 pound/acre iron applications from dry concentrate based sprays. The rapid decline in root growth from 0.0 pound iron per acre 27.5 Kg/50 sq.m. to an average for all other plots of 16/7 kg/50 sq.m., the average of all plots with iron added to the $N^6BA$/seaweed. No significant differences existed among the averages of extraction forces of any of the iron containing sprays regardless of wet or dry sources. There was a clear difference between the extraction forces required for the plots treated with sprays made from a concentrate of $N^6BA$ on dry seaweed and humic acid but no iron and others with iron or the control plot (which is lower than the extraction force required from the plots sprayed with a wet concentrate base, but not materially different from other dry based concentrate plots in which iron is included.

The overall lesson from the root mass study is that the presence of iron in molecular ratios of about 200:1 or greater substantially decreases root development which is perhaps the major morphological effect of $N^6BA$ on grasses.

The inference that iron and $N^6BA$ have a shared site of entry or reactivity into or within the grass plant is supported by these data. Further, since the molecular ratio is so disproportionate (100:1 at 0.5 pounds per acre), indicates that $N^6BA$ is very strongly attached to this likely common-site of physiological activity in turf grasses.

There are references suggesting that humic acids particularly the low molecular weight humic acids are capable of combining with plant root membranes and so combined acting as sites of ingress for even protein molecules.

The observation that humic acids increase iron uptake and that seaweed adds to this effect suggests that there is some likelihood that iron and $N^6BA$ complexes with a protein derived from seaweed and thence is transported across a root membrane. These data show an increase in the efficacy of fertilizer uptake and a decrease in the efficacy of $N^6BA$ in the presence of a large amount of ferrous iron ions.

Decreasing the molecular ratio between iron and $N^6BA$ will completely offset the inhibitory effect of high iron contents in spray solutions made from dry concentrates when the $N^6BA$ is applied as absorbed by drying upon dry powdered seaweed and humic acid. It is apparent that humic acid and/or seaweed materially enhances $N^6BA$ activity and fertilizer responses of plants when a proper balance molecular ratio of $N^6BA$ and the fertilizer is used.

Distinct advantages in $N^6BA$ response by plants are afforded by completing the $N^6BA$ on humic acids and seaweed as shown in the process illustrated in FIG. 5.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A plant growth promoter composition for regulation and promotion of the growth rate and characteristics of plants comprising N-6-Benzyladenine concentrated in a solubilizing agent comprising at least 1% of a water soluble organic hydroxy compound selected from the group consisting of glycerine, ethanol, methanol, ethylene glycol, polypropylene glycol, and propylene glycol, and a metal hydroxide-soluble in a water solution.

2. The concentrated plant growth promoter of claim 1, wherein the water soluble organic hydroxy compound is selected from the group consisting of ethanol, methanol, ethylene glycol, and polyethylene glycol.

3. The concentrated plant growth promoter of claim 1, wherein said organic hydroxy compound comprises an alcohol.

4. The concentrated plant growth promoter of claim of claim 1, said inorganic hydroxide comprises a monovalent cation.

5. The concentrated plant growth promoter of claim of claim 1, wherein said inorganic hydroxide comprises potassium hydroxide.

6. The concentrated plant growth promoter of claim of claim 1, wherein said inorganic hydroxide comprises sodium hydroxide.

7. The concentrated plant growth promoter of claim of claim 1, wherein said hydroxy compound comprises a glycol.

8. The concentrated plant growth promoter of claim 1, wherein said inorganic hydroxide comprises calcium hydroxide.

9. The concentrated plant growth promoter of claim 1, wherein said inorganic hydroxide comprises magnesium hydroxide.

10. The concentrated plant growth promoter of claim 1, wherein said inorganic hydroxide comprises zinc hydroxide.

11. The concentrated plant growth promoter of claim 1, including a mineral acid.

12. The concentrated plant growth promoter of claim 11, wherein said mineral acid is humic acid.

13. The concentrated plant growth promoter of claim 1, including a seaweed.

14. The concentrated plant growth promoter of claim 1, wherein said N-6-Benzyladenine solvent initially comprises at least 95% ethanol, and after dilution with water said plant growth promoter remains in solution at a normality of 0.0025.

15. The concentrated plant growth promoter of claim 1, including an iron salt.

16. The concentrated plant growth promoter of claim 1, including humic acid, seaweed, and ferrous sulfate heptahydrate.

17. A process of uniformly coating dry powdered humic acid and seaweed with a $N^6BA$ concentrate solution, comprising the steps of:

preparing a solution of $N^6BA$ concentrate solution comprising an alcohol, an alkaline metal hydroxide soluble in a water solution, and an iron salt;

applying said $N^6BA$ concentrate solution to a mixture of dry powdered humic acid and seaweed;

evaporating the residual alcohol through low temperature drying forming a caked material;

pulverizing the caked material to a powdered form; and suspending the finely powdered concentrate in an aqueous spray solution.

18. The process of uniformly coating dry powdered humic acid and seaweed with a $N^6BA$ concentrate solution of claim 17, further comprising the step of mixing said powdered concentrate with dry fertilizers for field application.

19. The process of uniformly coating dry powdered humic acid and seaweed with a $N^6BA$ concentrate solution of claim 17, further comprising the step of mixing said powdered concentrate with soluble fertilizer salts for liquid spray-applications.

* * * * *